(12) United States Patent
Nishiama et al.

(10) Patent No.: US 9,090,845 B2
(45) Date of Patent: Jul. 28, 2015

(54) PROCESS FOR PRODUCING HIGH-YIELD BIODIESEL APPLYING HIGH ACIDITY TRIGLYCERIDES WITH GENERATION OF GLYCERIN 90% FREE OF SALTS

(71) Applicant: Maria Aparecida Cirone Taboada ME, São Paulo (BR)

(72) Inventors: Hiromu Nishiama, Sao Jose dos Campos (BR); Silvio Antonio Cazzolato, Sao Jose dos campos (BR); Matheus Marchi dos Santos Silva, Piracicaba (BR)

(73) Assignee: GLYCEROSOLUTION QUIMICA LTDA, São Paulo-SP (BR)

( * ) Notice: Subject to any disclaimer, the term of this patent is extended or adjusted under 35 U.S.C. 154(b) by 3 days.

(21) Appl. No.: 13/748,281

(22) Filed: Jan. 23, 2013

(65) Prior Publication Data

US 2013/0185991 A1    Jul. 25, 2013

(30) Foreign Application Priority Data

Jan. 24, 2012  (BR) ...................... 10 2012 001584 6

(51) Int. Cl.
| | | |
|---|---|---|
| *C10L 1/18* | (2006.01) |
| *C11C 3/04* | (2006.01) |
| *C10L 1/02* | (2006.01) |
| *C11C 3/10* | (2006.01) |

(52) U.S. Cl.
CPC ............... *C10L 1/1802* (2013.01); *C10L 1/026* (2013.01); *C11C 3/04* (2013.01); *C11C 3/10* (2013.01); *Y02E 50/13* (2013.01)

(58) Field of Classification Search
None
See application file for complete search history.

(56) References Cited

U.S. PATENT DOCUMENTS

| | | | | |
|---|---|---|---|---|
| 4,698,186 | A * | 10/1987 | Jeromin et al. ................ | 554/174 |
| 6,288,287 | B2 * | 9/2001 | Ueoka et al. .................. | 568/869 |
| 7,806,945 | B2 * | 10/2010 | Jackam et al. .................. | 44/308 |
| 2011/0054200 | A1 * | 3/2011 | Cai et al. ....................... | 554/169 |

FOREIGN PATENT DOCUMENTS

| | | |
|---|---|---|
| BR | PI0703303-6 | 3/2009 |
| BR | PI0902550-2 | 11/2010 |

* cited by examiner

*Primary Examiner* — Yate K Cutliff
(74) *Attorney, Agent, or Firm* — B. Aaron Schulman, Esq.; Stites & Harbison, PLLC.

(57) ABSTRACT

Process for producing high-yield biodiesel applying high acidity triglycerides with generation of glycerin 90% free of salts starting from fatty lower cost fatty material allied with an esterification and innovative extraction process that generates a further value, more specifically for the production of biodiesel.

2 Claims, 5 Drawing Sheets

Figure 3 (con't)
Transesterification
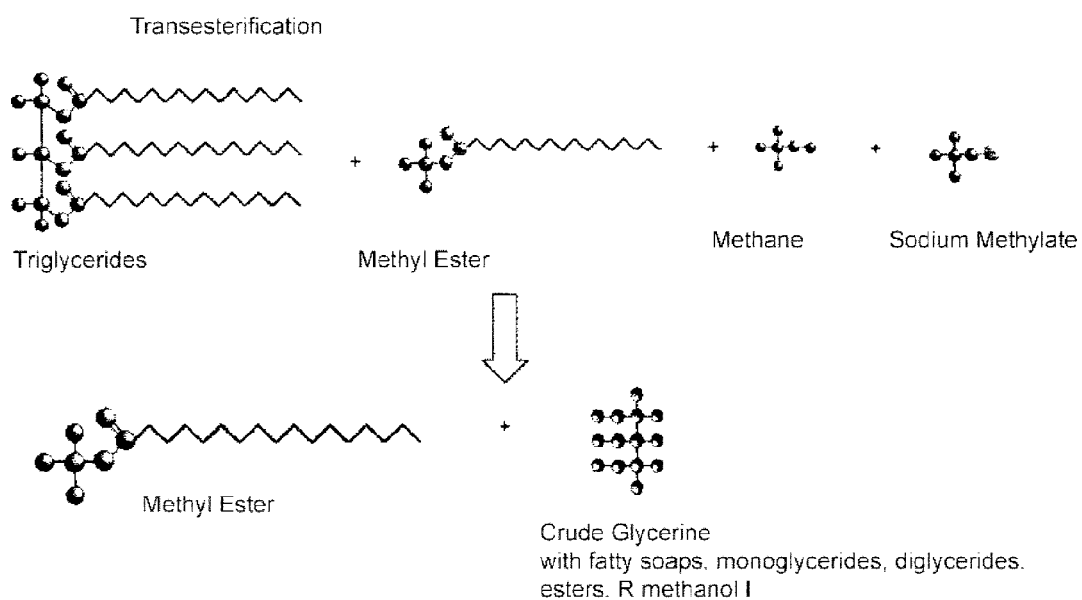
Triglycerides     Methyl Ester     Methane     Sodium Methylate
Methyl Ester
Crude Glycerine
with fatty soaps, monoglycerides, diglycerides. esters. R methanol I
Purification of glycerine
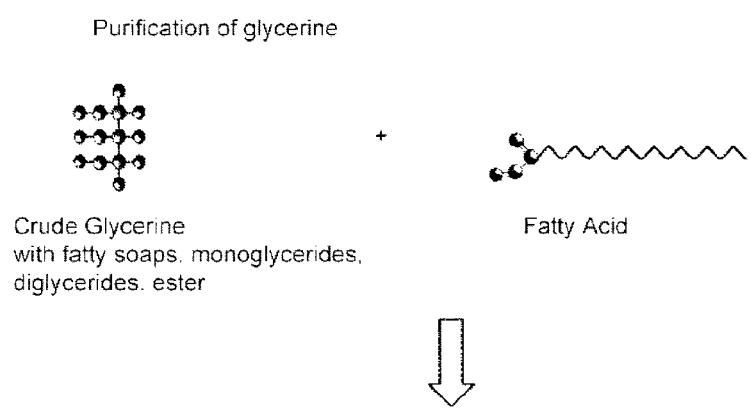
Crude Glycerine
with fatty soaps, monoglycerides,
diglycerides. ester
Fatty Acid Figure 3 (con't)
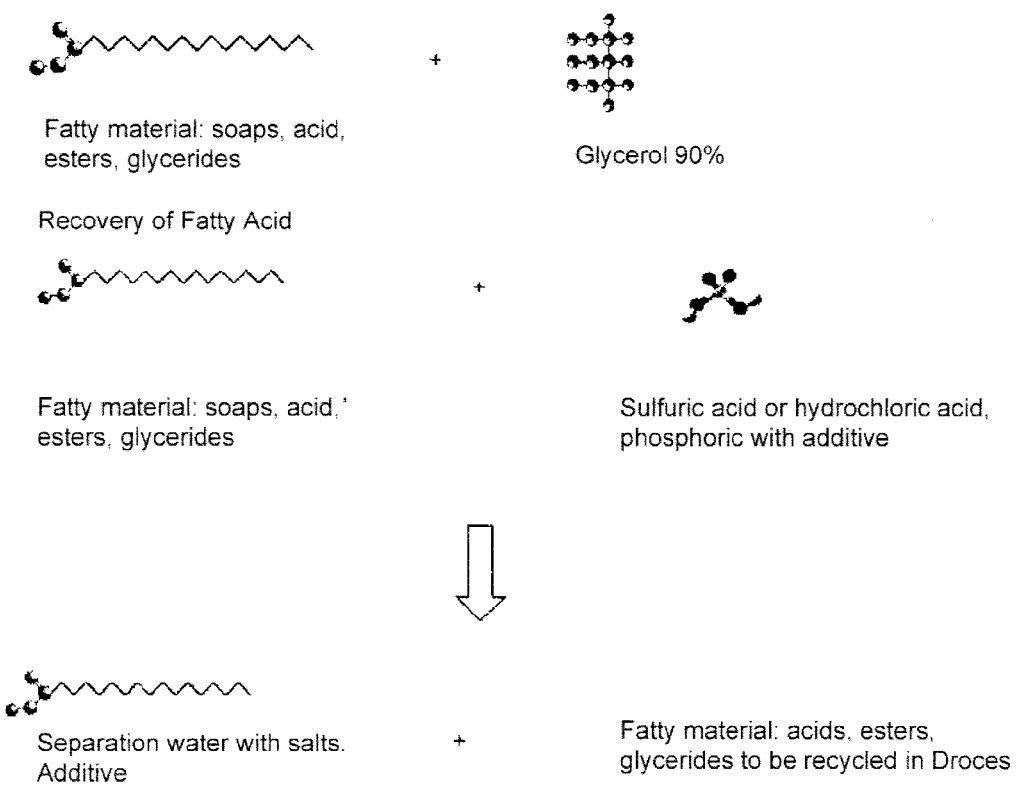

PROCESS FOR PRODUCING HIGH-YIELD BIODIESEL APPLYING HIGH ACIDITY TRIGLYCERIDES WITH GENERATION OF GLYCERIN 90% FREE OF SALTS

FIELD OF THE INVENTION

The present invention originates from the biofuels field, applies to the chemical industry in general as well as to the cosmetics industry. More specifically, the purpose of this invention comprises a process of producing methyl esters using low quality and low cost raw materials, with 100% yield of fatty material and at the same time producing 90% salt-free glycerin.

BACKGROUND OF THE INVENTION

The steady increase in demand for power sources, the climatic changes caused by heating of the atmosphere and the easily extracted oil reserves, along with a more intense socio-economic development, especially in developing nations, has provided incentive for the consumption of renewable resources, which can at least partially substitute fossil fuels such as oil, coal and natural gas.

Recently, biodiesel arose as a viable alternative in terms of renewable fuel. Transesterification is currently the most commonly used process in biodiesel production. It consists of a chemical reaction of vegetable oils or animal fats with common alcohol (ethanol) or methanol, stimulated by a catalyst, of which also extracts glycerin, a product with many different applications in the chemical industry.

Biodiesel may also be attained through other processes such as cracking and esterification. From a chemistry point-of-view, the oil or fat is used in the production of biodiesel is a triglyceride, that is, a tri-ester derived from glycerin.

Under the action of a basic catalyst and in the presence of methanol of ethanol, the oil undergoes transesterification, forming 3 methyl ester or ethyl molecules from the fatty acids, which constitute biodiesel in its essence, and liberating one molecule of glycerol or glycerin. Dozens of plant species may be used for the production of biodiesel, such as castor, palm, sunflower, babassu palm, peanut, soybean and jatropha, among others, as well as animal fats (e.g., tallow) or vegetable.

The processes for biodiesel production generally have a maximum mass yield of 95%, primarily depending on the quality of the fatty material. The better the quality, the higher the yield. Generally, the higher quality raw materials are more expensive, making biodiesel production economically unfeasible. The low mass yield is another economically negative aspect that ends up impacting the business profitability.

Triglycerides with high acidity are normally esterified prior to proceeding with the transesterification step. The process of esterification is a costly step because it requires that the excess methanol used and the reaction water be eliminated via the process of distillation, which increases the cost of the production process.

Crude glycerin coming from the current process lose around 5% to 10% of fatty material in form of 25 esters, partial glycerides and soaps, hence the final yield is around 95% at most. To separate the fatty material contained in crude glycerin, inorganic acids are usually added, such as sulfuric acid or hydrochloric acid, with the formation of their respective salts.

The glycerin generated has a purity of 60 to 80%, however the major drawback is the presence of inorganic salts like sodium sulfate and sodium chloride, which makes the glycerin purification process costly and introduces corrosion problems in the equipment used to distill the glycerin. The use of this glycerin as such is very limited due to the presence of these salts. Besides this productive aspect, a large amount of solid residue is formed, which needs to be discarded into the environment. With all these negative aspects, the value of this glycerin is marginal, and currently is a problem for major biodiesel producers.

STATE OF THE ART

A brief query into the data bases concerning documents that support the understanding of the present invention, some processes are reported, such as Brazilian document no. PI 0603857 (UNICAMP) includes the production of alkyl esters, such as Biodiesel, from any vegetable oil or animal fat, methyl or ethyl routes, catalyzed by a strong modified base, either in the homogeneous layer, which provides a higher yield, or the transesterification reaction, promoting spontaneous sedimentation of glycerin. After the removal of excess alcohol from the reaction medium, the naturalization of the catalyst and its purification, esters (biodiesel) are obtained with purities of greater than 99%. The catalysts of the present invention allow both the batch and the continuous processes, where all the engineering of the industrial plants that already operate with Methanol can be used in the ethyl course. The catalysts in the heterogeneous layer simplify the process, because they do not contaminate the products. As a result, the alkyl ester neutralization and purification steps are not needed, and are not consumed during the transesterification process.

Another document, no. PI 0703303-6 (Instituto Nacional de Tecnologia—INT) refers to a process for obtaining Biofuels, starting from solid or liquid triacylglycerides at room temperature, with different average molecular weights and degrees of maturation, of vegetal or animal origin, crude or refined, mono alcohols of different molecular weights, and homogeneous or heterogeneous molecular catalysts. This invention is characterized by the introduction of Diesel, kerosene and/or its mixtures available on the national and international market, into the reaction medium. In addition to this, the invention provides a reduction of viscosity of the reaction medium, increasing the speed and the conversion yield, facilitating the separation of glycerin and the alcohol residue and the catalyst employed, and generally favors obtaining products more in line with the respective specifications for Biodiesel B 100.

Another Brazilian document no. PI 0902550-2 (SENAI) describes a practical purification method of white glycerin, arising from biodiesel production, free from distillation at a reduced pressure and without the need for neutralization of the medium through chemical agents classified as organic or inorganic bases. In the present purification process, acetyls and ketals are produced from the cyclization of the corresponding triol in the presence of different aldehydes and ketones in the absence of additional acid catalysts, the cyclized adducts are hydrolyzed in different concentrations of distilled water and the glycerin is recovered with a degree of purity varying from 90 to 99.9%, and the chemical yield is quantitative.

SUMMARY OF THE INVENTION

To eliminate the drawbacks mentioned above, and more specifically, to provide direct production of glycerin 90% free of inorganic salts, with esterified material from soybean oil, palm oil, cotton, canola, sunflower, linseed, castor oil plant and tallow, with an acidity index of approximately 30 mgKOH/g, where the primary innovative aspects of this patent are:

a—use of high acidity raw materials and an esterification process that does not require the distillation of methanol and water prior to the transesterification process;
b—a process with 100% yield on the fatty material;
c—a process producing glycerin 90% free of inorganic salts.

The present process for obtaining biodiesel at high yield and flexibility is based on the following mixtures applied to the new innovative process:

First mixture: low quality fat raw material having with a maximum acidity index of 30 mgKOH/g, 30% methanol, MW catalyst are loaded into the reactor. The purpose of this step is the esterification of the free fatty acids prior to proceeding to the transesterification step;

Second mixture: Esterified Fatty Material, methanol, sodium methylate and water. The purpose is to take advantage of the benefits afforded from the previous process, which are the increase in the conversion of transesterification, reduction in the soap generated and less loss of fatty material in the crude glycerin;

Third mixture: Fatty Acid, Crude Glycerin, soap, ester and salts. The purpose is to perform the extraction of all fatty material contained in the crude glycerin, which are the soaps, monoglycerides, diglycerides, esters, using the same fatty acid generated by this process. Crude glycerin, which is a homogenous mixture, with the addition of the extraction agent, separates into two layers, upper layer, which contains the fatty materials previously contained in the crude glycerin, and the lower layer, which contains 90% to 95% pure glycerin;

Fourth mixture: Fatty acid, soap, ester, glycerin, water, additive and sulfuric acid. The purpose is to hydrolyze all the soap to recover it in its fatty acid form, and to use the additive that is a tensoactive that assists in the removal of polar compounds generated during the breakdown of soaps through sulfuric, hydrochloric, phosphoric, citric, lactic, acetic, and formic acid.

The benefits of the present process are observed in the esterification step where the excess methanol allows for a quick conversion of free fatty acids and the removal of an excess of methanol by physical separation, without using distillation, using basic equipment. The process affords multiple benefits because the separated methanol contains most of the esterification water formed and also extracts most of the substances that confers a dark color onto the fatty materials. Thus, the final product has a lighter color and higher quality.

Another important feature of the present invention is the removal of these polar substances that make the subsequent processes; such as transesterification, separation, washings, and filtration; much simpler and quicker, reducing the small losses at each step. The saves in energy and the lower emissions to the environment are also very important features.

In the glycerin purification step the present application follows a path distinct from the current purification methods in that it does not use chemical reactions and takes advantage of the molecular interactions between glycerin, soap, ester and fatty acid, since, in the present process, the contaminants are soap, ester and possible phosphate or sulfate salts. The fatty acid acts as a solvent for the contaminants, extracting the contaminants and providing a glycerin with a high degree of purity.

The most difficult step is extracting the maximum quantity of pure glycerin without carrying soaps and other fatty materials, such as monoglycerides, diglycerides or even biodiesel.

Moreover, the success of this step was finding the optimal ratio between the extracting solvent (recovered fatty acid) and the crude glycerin at an appropriate temperature level that allows, first the extraction of glycerin and then the physical decanting of the same, thus separating it from the fatty materials layer (soaps, glycerides, esters and fatty acids).

The purpose, therefore, of the present invention is to provide a process that allows for the use of low quality primary materials such as, for example, fats and hydrolyzed oils, frying oils, recovered fatty acids that cost much less than the high quality raw materials, such as refined soybean oil, refined palm oil and clarified tallow from meat processing plant.

It is the purpose of this invention to anticipate that the consumption of reagents such as methanol and the catalyst is lower when compared to the current processes.

Another objective achieved pertains to the substantial energy savings using the process due to not needing distillation or the recovery of large quantities of methanol.

The present invention also seeks to provide that the process is performed on multipurpose equipment; routinely existing in the chemical industry and the construction of equipment specifically for the production of biodiesel is not necessary.

Furthermore, this invention anticipates that the glycerin produced as a byproduct in this process has a high degree of purity, that is, greater than 90%, which facilitates further purification processes to reach the pharmaceutical cosmetics degree of 99.99%. This invention also anticipates that it can be used directly without the need for prior purification in industrial applications such as, for example, the production of alkyd resins, as an alternative fuel without the generation of ashes, and more recently as a carbon source for feed and biotechnical fermentation processes that have salt limits, which limits used of traditional glycerin that have a high salt content.

Another purpose of the present invention pertains to the fact that this glycerin, with a purity of greater than 90% is free of inorganic salts, will help make the production processes currently under development more economically viable and make them faster, such as, for example, the production of acrylic acid, 1,2 propanodiol, polyglycerin, epoxy resins and surfactants based on polyglycerin.

Another objective achieved by the present invention is that the innovative process makes the production of biodiesel and glycerin more sustainable from environmental and energy consumption points of view.

Another objective pertains to the fact that in the present innovative process the fatty acids, initially in the form of soaps, are totally recycled back into the process or as an extraction agent and/or mixed into the process fatty material for the production of biodiesel, resulting in 100% usage of the fatty material.

DETAIL DESCRIPTION OF THE INVENTION

Figure 1:
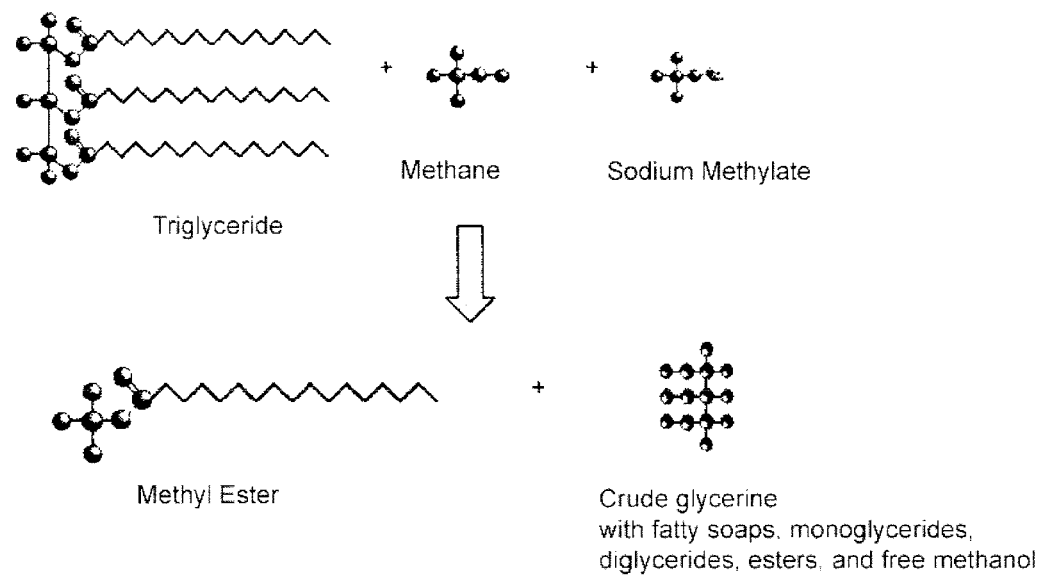
FIG. 1 represents the conventional Process of obtaining Biodiesel (high quality raw material) through the direct reaction of transesterification.
Figure 2:
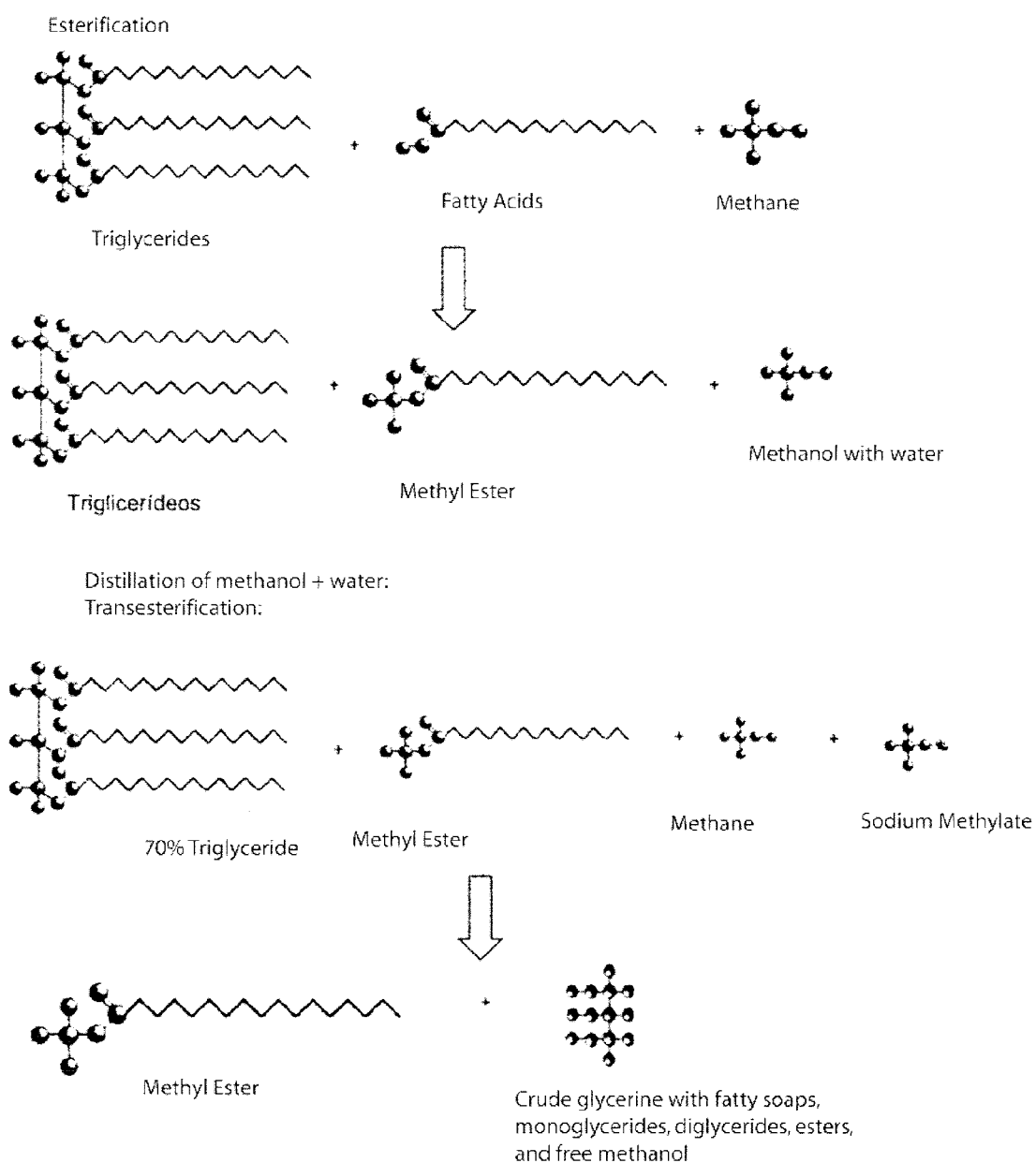
FIG. 2 represents the conventional process of obtaining Biodiesel (low quality raw material), showing the steps of esterification, transesterification, the process of breaking down soap in the crude glycerin and, consequently, the generation of glycerin with salts and the recovered fatty acid layer.
Figure 3:
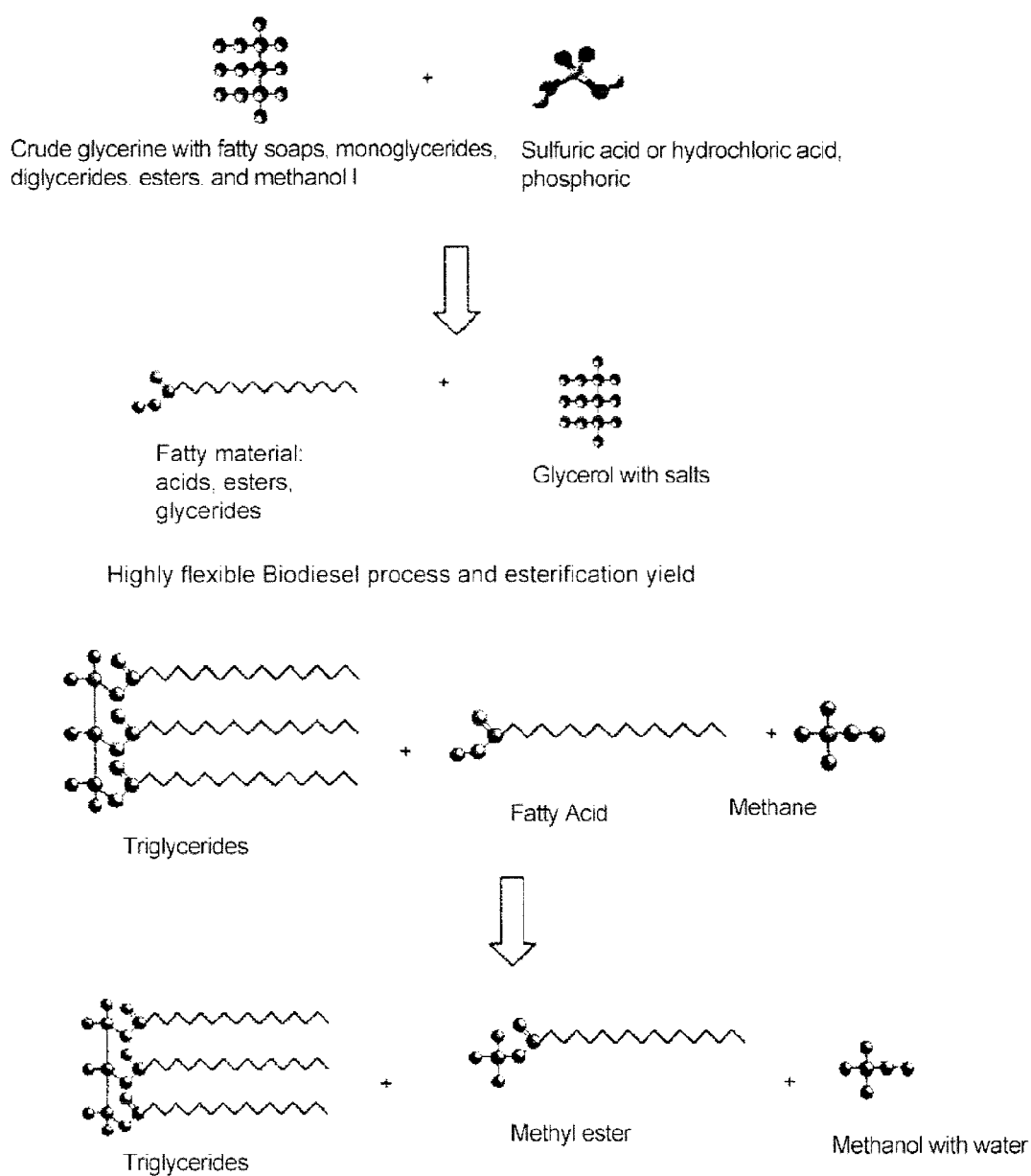
FIG. 3 represents the steps obtained in the high flexibility and yield Biodiesel Process.

The purpose of this invention pertains to the field of biofuels, if extended to the chemicals industry in general and the cosmetics industry through the innovative highly flexible process that allows the use of low quality raw materials with a maximum acid index of to 30 mgKOH/g and at the same time produce a glycerin with a 90% purity, free of salt. For such, follow the following steps:

(a) Add to esterified material 30% mass/mass methanol and 0.25% mass/mass catalyst MW at a temperature of 55° C. and under stirring, until the acid index reaches a value less than 2 mgKOH/g; the time varying between 90 and 120 minutes;

(b) Then, stop the stirring, and wait 30 minutes; there will be a separation of the layers, with the upper layer predominantly composed of methanol, having from 85 to 90% mass/mass and this layer is dark; the lower layer is predominantly formed by fatty esterified material that will vary between 83% and 88% mass/mass and where this second layer is light brown;

(c) The lower layer follows to the next layer, of the transesterification, heated to a temperature of 60° C. and, after the addition of sodium methylate, the temperature is slowly reduced to 5° C.; the reaction follows in the receptacle, stirred and heated until the combined glycerin reaches a value less than 0.25% mass/mass;

(d) Stop stirring and wait 30 minutes for the formation of the 2 layers, which are, the upper biodiesel layer with 98% conversion and the lower crude glycerin layer with 60 to 65% glycerol, and humidity of 0.5 to 1% mass/mass and 25% methanol; then go on to removal of methanol in the simple and already known distillation procedure;

(e) Treatment step of the crude glycerin arising from steps "a" to "d" of this procedure, with the said treatment step able to be applied to glycerin originating from other processes where fatty raw material is used in the presence of fatty acid;

(f) Then, add fatty acid, with an acid index between 150 and 160 mgKOH/g, at 80° C. already being stirred; only after adding all the fatty acid, slowly add the crude glycerin, for 15 minutes at 80° C.; hold at the said conditions for half an hour and, after this time, stop stirring;

(g) Allow it to settle for 30 minutes, and in this period there will be separation of layers, and where the upper layer is predominantly composed of fatty acid, but it also contains soap, ester, sulfates, chlorides and phosphates; the lower layer is largely composed of glycerin, around 95% glycerol containing 2% soap and a humidity of 1.5 to 2% mass/mass;

(h) Then, the upper layer becomes a split of soap so that all the fatty acid can be recovered, thereby making use of an additive solution so that the sulfuric acid aids in the formation of sulfonates and an increase in pigments is softened;

(i) The upper layer is then added at 80° C. to a stirred and heated container; soon after adding an additive solution containing non-ionic surfactant at 1% and at room temperature; after the addition of additive solution, 98% sulfuric acid is slowly added over 15 minutes, in order to hydrolyze all the soap present; the pH of the reaction medium reaches 3.5 and stays at 80° C. under stirring for another 30 minutes, and (j) Stop the stirring and allow to settle for 30 minutes at a temperature of 80° C., and there will be a formation of two distinct layers, the upper layer composed of fatty acid and ester with a humidity of around 1% mass/mass. The lower layer is formed of water, additive, glycerin, sulfates and sulfonate compounds.

This process may result in individualized and family products, such as: (i) Biodiesel, methyl esters for industrial use (solvents for formulation for agricultural use); and (ii) 90% Glycerin, and its derivatives (USP grade glycerin, 1,2 propanodiol, polyglycerin esters of polyglycerin, alkyd resins, epoxy resins, hydrogen source.

Although the present invention may be susceptible to different modalities, a preferred modality with an understanding that the present description should be considered an exemplification of the invention principles was shown in the drawings and in the detailed discussion, and it does not intend to limit what was illustrated and described herein.

The invention claimed is:

1. A process for producing high-yield biodiesel applying high acidity triglycerides with generation of glycerin 90% free of salts, the process comprising the steps of:

(a) providing an esterified material with an acidity index of about 30 mgKOH/g;

(b) adding methanol at a ratio of from 20% to 40% mass/mass and a catalyst MW at a ratio of from 0.1% to 0.5% mass/mass to the esterified material at a temperature ranging from 45° C to 65° C, providing a mixture of esterified material and methanol; stirring the mixture of esterified material and methanol until the acidity index reaches a value less than 2 mgKOH/g; for a period of time from 60 minutes to 240 minutes;

(c) stopping the stirring for 30 minutes, allowing for the mixture of esterified material and methanol to separate, wherein a first upper layer is dark and is predominantly composed of methanol, water and coloring agents; and a first lower layer is light brown and primarily esterified fatty material and solubilized methanol;

(d) transesterificating the first lower layer, wherein methanol is added to the mixture of esterified fatty material and methanol, providing a mixture of esterified fatty material and methanol with added methanol to correct the esterified methanol ratio to 15% mass/mass; heating the mixture of esterified material and methanol with added methanol to a temperature of from 50° C. to 60° C.; adding sodium methylate; providing a mixture of esterified material and methanol with added methanol and sodium methylate; and containing the mixture of esterified material and methanol with added methanol and sodium methylate in a stirring and heating container until a mixed glycerin reaches a value lower than 0.25% mass/mass;

(e) stopping the stirring for 30 minutes, allowing for the mixture of esterified material and methanol with added methanol and sodium methylate to separate, wherein a second upper layer is of biodiesel with 98% conversion and a second lower layer is of crude glycerin, from 50% to 65% glycerol, containing free methanol, fatty material selected from the group consisting of: soaps, esters, glycerides, moisture and mixtures thereof; distilling the second lower layer to remove the free methanol;

(f) treating the crude glycerin originating from steps (b) to (e);

(g) adding fatty acid to the second upper layer mixture of esterified material and methanol with added methanol and sodium methylate, with an acidity index ranging from 80 mgKOH/g to 210 mgKOH/g, at a temperature ranging from of 60° C. to 95° C. already being stirred;

and adding the crude glycerin, stirring and maintaining the same reaction conditions for 30 minutes;

(h) stopping the stirring for 30 minutes, allowing for the second upper layer mixture of esterified material and methanol with added methanol and sodium methylate and fatty acid and crude glycerin to separate, wherein a third upper layer of the second upper layer mixture of terified material and methanol with added methanol and sodium methylate and fatty acid and crude glycerin is fatty material containing soap, ester, glycerides, and residual glycerol; and a third lower layer is glycerin about 95% glycerol, containing residue soap and moisture, the glycerol content depending on the water content and residue free methanol in the crude glycerin;

(i) the third upper layer undergoing a split of soap so that all the fatty acid is recovered, by using an a first additive solution to reduce the effect of sulfuric acid on the formation of sulfonates and other agents that confers color to the recovered fatty layer;

(j) adding the third upper layer to a stirring and heating container at a temperature ranging from 50° C. to at 80° C.; and then adding a second additive solution containing a non-ionic surfactant at 1% and at room temperature; and slowly adding sulfuric acid 98%, hydrolyzing the soap, and (k) stopping the stirring for 30 minutes at a temperature of 80° C., allowing for the third upper layer of the mixture of esterified material and methanol with added methanol and sodium methylate and fatty acid and crude glycerin to separate, wherein a fourth upper layer is fatty acid and ester with a moisture of about 1% mass/mass; and a fourth lower layer is water, additive, glycerin, sulfates and sulfonate compounds which are sent to effluent treatment.

2. The process according to claim 1, wherein the esterified material is from the group consisting of: soybean oil, palm oil, cotton, canola, sunflower, linseed, castor oil plant and tallow.

* * * * *